United States Patent [19]

Morita

[11] Patent Number: 5,314,442
[45] Date of Patent: May 24, 1994

[54] BLOOD COLLECTING APPARATUS

[75] Inventor: Susumu Morita, Nishinomiya, Japan

[73] Assignee: APLS Co., Ltd., Okayama, Japan

[21] Appl. No.: 997,337

[22] Filed: Dec. 28, 1992

[30] Foreign Application Priority Data

Oct. 26, 1992 [JP] Japan .................................. 4-287287

[51] Int. Cl.$^5$ .............................................. A61B 17/32
[52] U.S. Cl. .................................................... 606/182
[58] Field of Search .................. 128/770; 606/181-183

[56] References Cited

U.S. PATENT DOCUMENTS

| | | | |
|---|---|---|---|
| 3,358,689 | 12/1967 | Higgins | 606/181 |
| 4,375,815 | 3/1983 | Burns . | |
| 4,379,456 | 4/1983 | Cornell et al. . | |
| 4,388,925 | 6/1983 | Burns . | |
| 4,414,975 | 11/1983 | Ryder et al. . | |
| 4,416,279 | 11/1983 | Lindner et al. . | |
| 4,442,836 | 4/1984 | Meinecke et al. . | |
| 4,449,529 | 5/1984 | Burns et al. . | |
| 4,452,243 | 6/1984 | Leopoldi et al. . | |
| 4,462,405 | 7/1984 | Ehrlich . | |
| 4,503,856 | 3/1985 | Cornell et al. . | |
| 4,514,609 | 4/1985 | Fricke et al. . | |
| 4,527,561 | 7/1985 | Burns . | |
| 4,535,769 | 8/1985 | Burns . | |
| 4,539,988 | 9/1985 | Shirley et al. . | |
| 4,545,376 | 10/1985 | Beiter . | |
| 4,553,541 | 11/1985 | Burns . | |
| 4,577,630 | 3/1986 | Nitzsche et al. . | |
| 4,580,564 | 4/1986 | Andersen . | |
| 4,580,565 | 4/1986 | Cornell et al. . | |
| 4,616,649 | 10/1986 | Burns . | |
| 4,624,253 | 11/1986 | Burns . | |
| 4,648,408 | 3/1987 | Hutcheson et al. . | |
| 4,653,513 | 3/1987 | Dombrowski . | |
| 4,658,821 | 4/1987 | Chiodo et al. . | |
| 4,676,244 | 6/1987 | Enstrom . | |
| 4,677,979 | 7/1987 | Burns . | |
| 4,712,548 | 12/1987 | Enstrom . | |
| 4,715,374 | 12/1987 | Maggio . | |
| 4,735,203 | 4/1988 | Ryder et al. . | |
| 4,738,261 | 4/1988 | Enstrom . | |
| 4,794,926 | 1/1989 | Munsch et al. . | |
| 4,817,603 | 4/1989 | Turner et al. . | |
| 4,844,095 | 7/1989 | Chiodo et al. . | |
| 4,856,515 | 8/1989 | Turner et al. . | |
| 4,858,607 | 8/1989 | Jordan et al. . | |
| 4,869,249 | 9/1989 | Crossman et al. . | |
| 4,889,117 | 12/1989 | Stevens . | |
| 4,892,097 | 1/1990 | Ranalletta et al. . | |
| 4,924,879 | 5/1990 | O'Brien . | |
| 4,990,154 | 2/1991 | Brown et al. | 606/182 |
| 4,994,068 | 2/1991 | Hufnagle . | |
| 4,995,402 | 2/1991 | Smith et al. . | |
| 5,026,388 | 6/1991 | Ingalz . | |
| 5,047,044 | 9/1991 | Smith et al. . | |
| 5,074,872 | 12/1991 | Brown et al. . | |
| 5,100,427 | 3/1992 | Crossman et al. . | |
| 5,105,823 | 4/1992 | Blum | 606/181 |
| 5,133,730 | 7/1992 | Biro et al. . | |
| 5,147,375 | 9/1992 | Sullivan et al. . | |

FOREIGN PATENT DOCUMENTS 3-30757   3/1991   Japan .

OTHER PUBLICATIONS

Lagana, "Guide to Finger-Pricking Equipment," *Diabetese Self-Management* (R. A. Rapaport Publishing, Inc.), 7, 6-11 (Jul./Aug. 1990).

Primary Examiner—Max Hindenburg
Attorney, Agent, or Firm—Leydig, Voit & Mayer, Ltd.

[57] ABSTRACT

A blood-collecting apparatus comprises a lancet assembly composed of a lancet body and a protector, with the lancet body having a needle end which is protected by the protector. The apparatus further comprises a pricking device and an end cap, with the device separably holding the lancet body, while the end cap being formed with an opening through which the needle end can advance back and forth. The lancet body has a first locking means and an arm means corresponding to a first lockable means and a second lockable means of the end cap, respectively. The apparatus is easy to use, and those means cooperate with one another to eliminate the infection or other hygienic problems when taking a blood sample and also to render the used apparatus safely disposable.

8 Claims, 5 Drawing Sheets

BLOOD COLLECTING APPARATUS

BACKGROUND OF THE INVENTION

1. Field of the Invention

The present invention relates to an apparatus used to collect human blood samples, and more particularly, relates to a blood collecting apparatus of the so-called pricking type which comprises a lancet and an end cap cooperating with the lancet.

2. Description of Prior Art

The number of diabetics is increasing worldwide, and the governmental or other organizations of many countries are making best efforts to establish a system f or earlier detection of diabetes. In general, the blood sugar test is necessary for the early detection. Owing to the recent rapid progress in electronics, the blood testing apparatuses and reagents for use to obtain the data relating to diabetes and other diseases have been made more compact, simpler and cheaper. Thus, the blood sugar test can now be conducted by people even in their houses, if so wanted. Since it is very difficult for a person to take his or her own blood sample for that test from his or her earlobe, the blood sample is usually taken from a fingertip.

"Finger-pricking devices" are widely used in hospitals and houses in order to take blood samples. Each of such devices comprises a throw-away lancet having a pointed needle end designed to pierce the fingertip (or other body portion, but the piercing of fingertip being the most cases). There have been proposed many types of such devices with the lancets.

Figure 9:
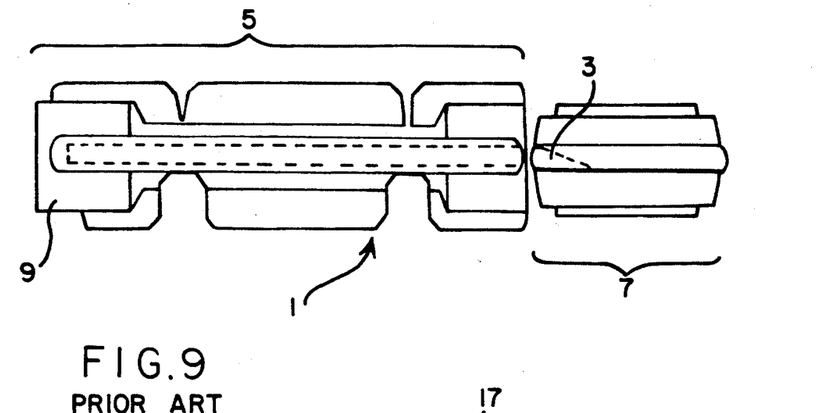
FIG. 9 is a side elevation diagrammatically showing a prior art lancer.

The lancets of this kind made by, for example, Bayer A. G. (Germany), Miles Incorporated (U.S.A.) and Life Scan Corp. (U.S.A.), are commercially available. FIG. 9 of the accompanying drawings schematically shows a prior art lancet 1 incorporated in the finger-pricking device, and FIG. 10 also illustrates in outline the finger-pricking device 11.

The operation when the device or lancet is used will now be described referring to FIGS. 9 and 10.

The lancet 1 shown in FIG. 9 comprises a lancet body 5 and needle protector 7, wherein the lancet body has a pointed needle end 3 projecting to pierce the fingertip, while the protector being a guard covering the needle so as isolate it from the outside. The lancet body 5 is a one-piece molded plastics member integral with the protector 7. The projecting needle end 3 is received in and shielded by the plastics material forming the protector.

The lancet body 5 may be wrung relative to the protector 7 so that the former is separated from the latter (in the so-called "twisting-off" manner). An end 9 of the thus separated lancet body 5 will then be secured to a lancet holder 13 formed in a lancet ejector 21 of the finger-pricking device 11. This ejector 21 is linked to a spring means (not shown) which comprises a spring lockable in its compressed state by an appropriate mechanism. After setting the lancet body 5 on the finger-pricking device, an end cap 16 will be fitted thereon so that its end deck 19 can be pressed to fingertip 17.

Figure 10:
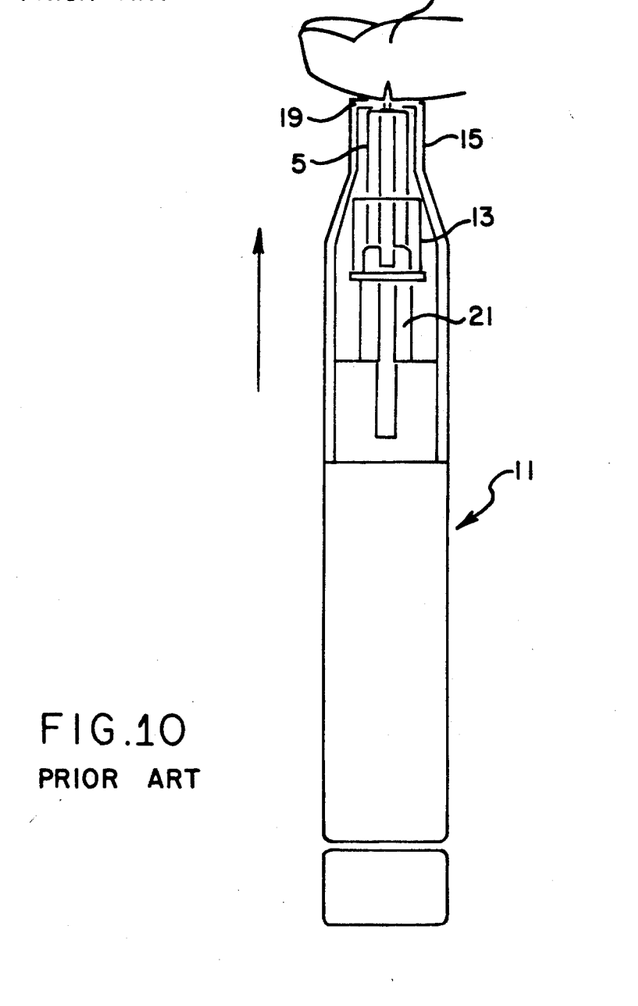
FIG. 10 is another side elevation showing the prior art lancet in use.

Then the locked spring will be released to take its uncompressed position, thus springing out the lancet body 5 towards the end deck of the end cap 15 (as indicated by the arrow in FIG. 10). The fingertip 17 is pierced in this way. In detail, the pointed needle end 3 forms a small cut in the fingertip. A little amount of blood oozing from the little cut will be collected for various tests. FIG. 10 shows an instantaneous state of the pointed needle end 3 piercing the fingertip 17. Subsequent to this instant, the lancet body 15 whose needle end 3 has pricked the fingertip will automatically be retracted a little distance towards its home position, and will take a position where said needle end 3 is spaced apart from the cut surface of the fingertip.

In the described manner of collecting the blood sample by means of the lancet of the finger-pricking device, the lancet body 5 is replaced with a new one after every operation. However, the end cap 15 of the finger-pricking device remains unreplaced. The end cap, particularly its end deck 19 which has contacted the skin of fingertip as shown in FIG. 10 can hardly be removed therefrom without being stained with the blood oozing from the tested person. In a case wherein a throughhole formed through the end deck for passing the needle is small and tight, the possibility of the contamination of end deck will be much higher.

There may be another case wherein one and the same finger-pricking device is used in common by some persons. One of them may be apt to use it only by replacing the lancet body but without sterilizing the end deck 19 of the end cap. In such an event, the small cut in his or her fingertip is very likely to come into contact with the blood of the other persons who have used that device to take their blood samples. If said other persons were carriers of AIDS virus or B-virus of hepatitis, the one person who thereafter uses the same device would possibly be infected with the virus of said disease. Thus, the finger-pricking device must be used with the greatest possible care. Further, there is another problem that the sticking or residual blood of a person who used the device before another person would occasionally be mixed with the newly taken blood sample to thereby disable accurate blood tests.

The end cap of the finger-pricking device may be renewed every time when a blood sample is taken, in order to avoid such an infection or contamination. According to a proposal which was made, the lancet is built in each end cap when it is manufactured. This end cap with its internal lancet will be replaced with a new one whenever used for sampling of blood. An example of blood sampling devices of this type is disclosed on the Patent Laying-Open Gazette Hei. 3-30757 and are put in the market by Miles Corporation (U.S.A.). This proposed device is however somewhat complicated and sophisticated in its structure so that its higher price would cause an additional expense to users.

The finger-pricking device shown in FIG. 10 will bring about a still further problem when it is used. After used to take a blood sample, the end cap 15 has to be removed to expose the lancet body 5 in order to manually detach it from the lancet holder 13. The needle end 3 thus exposed will possibly pierce the skin of an operator removing the lancet body 5, or come into contact with his or her wound. The blood which has oozed out of a patient and is sticking to the needle end will cause the aforementioned virus infection between the operator and the patient, if they are not the same person (as is the case in the tests carried out within a hospital).

It is a still another problem that, when the blood-stained lancets are discarded as they are, the needle ends may cause a danger of injuring those who handle same, also resulting in the infection of virus.

SUMMARY OF THE INVENTION

An object of the present invention, which was made in view of the aforementioned problems, is therefore to provide a lancet or apparatus which is easy to use, free from any hygienic problem such as the infection when taking a blood sample, and also can be discarded safe after use.

This object is achieved in the present invention by providing a blood collecting apparatus which comprises in general: a lancet comprising a lancet body and a protector, with the lancet body having a protruding needle end which is received and protected by the protector; a pricking device holding in place the lancet body in such a state that the needle end can be ejected to pierce a human body portion from which a blood sample is to be taken; an end cap having opposite ends and securable at one of the ends to the pricking device such that the lancet body on said device is kept in position to take in the blood sample, the end cap also having at its other end an opening through which the needle end can advance outward when the lancet is ejected; the lancet body comprising a first locking means and an arm means, whereas the end cap has an inside formed with a first lockable means cooperatable with the first locking means as well as a second lockable means cooperatable with the arm means; the locking and lockable means and the arm means being shaped such that, with the lancet body being attached to the pricking device and when covered with the end cap so as to be ready for the blood collecting, the first locking means of the lancet body snaps ahead and over the first lockable means of the end cap to thereby take its position therein, wherein the arm means is elastically yieldable to be deformed to allow the needle end of the ejected lancet body to pierce the human body portion; and the locking and lockable means and the arm means being also configurated such that, after the blood collecting, the arm means elastically recovers its undeformed home position so as to bear upon the second lockable means, thereby preventing the needle end from taking its exposed position out of the opening at the other end of the end cap, wherein the first locking means cooperates with the first lockable means in such a manner that the lance body is prevented from slipping off the end cap through the one end thereof, and thus is held in place within the end cap.

As will now be apparent, the blood collecting apparatus in the present invention is basically composed of three parts, that is the lancet, the pricking device and the end cap. Their structures will be described below in more detail.

The lancet of the blood collecting apparatus in the invention comprises the lancet body and the protector for the needle end. The lancet body itself comprises a needle having a diameter of about 0.5–0.8 mm adapted to pierce a human body portion where a blood sample is to be taken. The pointed needle end of said needle protrudes by a certain distance, for example about 3.1–3.3 mm, which distance is suited to pierce the body portion.

The lancet needle employed in the present invention is of such a shape as adapted to form a small cut or wound in a person's body portion so that the blood oozing therefrom may be collected for his or her blood test. Thus, the needle may be any one of the known conventional types which have been employed and combined with the pricking devices. For example, it may has such an acute end as disclosed on Japanese Patent Laying-Open Gazette Sho. 60-63040. The lancet body in the invention carries the needle so that at least the acute end thereof is exposed.

The lancet body has also a fixing means effective to fix the lancet body on the pricking device. The fixing means may preferably be positioned at or near the body's end opposite to the needle. The pricking device generally comprises an ejecting means which holds and ejects the lancet body. Therefore, the ejecting means has a holding portion, which cooperates with the fixing means to attach the lancet body onto said device. As described above regarding the prior art, each of the commercially available finger-pricking devices are designed such that the lancet body can be snapped on the holding portion of the ejecting means. Accordingly, the lancet body in the invention need not be specially designed insofar as it can be fitted in the holding means. In other words, it suffices that the lancet body's end (that is, the fixing means located there) is of such a dimension relative to the holding portion of the device's ejecting means that they can be "press-fitted" to each other.

The lancet body in the apparatus of the present invention has the first locking means and the arm means which all respectively engageable with the first and second lockable means formed on the inner surface of the end cap. Details of this structure will be given hereinafter.

The lancet of the apparatus is formed with the protector, which protects and isolates the protruding needle end from outside articles so as to prevent it from becoming contaminated with any foreign substance, until the lancet body is mounted on the pricking device.

The needle end of the unused lancet is located inside (i.e., inserted in, embedded in, forced through or otherwise held in) the protector, and therefore at least the acute extremity or preferably the entirety of the needle end projected from the lancet body is kept safe. In order to protect or isolate the entirety of said needle end from the outside, the protector may preferably be integral with the lancet body. Any appropriate plastics including a polyethylene and a polypropylene may be used to mold the lancet body integral with the protector, desirably in such a state that they can be "twisted off" one another.

In a preferable embodiment of the invention, the protector has a lug integral therewith and fittable in the opening of the end cap when the needle end advances through said opening to take a blood sample. The lug may be a protrusion of such a shape and size as being snapped in the opening of said end cap.

Any of the commercially available "finger-pricking devices" suffices as the pricking device in the apparatus of the invention. Those conventional pricking devices are constructed such that the lancet body is held in place and can be ejected towards a human body portion from which the blood sample is taken. In detail, the pricking device comprises the ejecting means with a portion holding the lancet body, which or whose end may preferably be "pressfitted" in the portion.

The ejecting means may generally be incorporated in combination with a suitable resilient member which acts to eject the lancet body attached to the device. The resilient or spring member is locked in its compressed state before ejection the lancet body, but can be released to take its uncompressed state to thereby forces said body towards a person's body portion. Upon piercing it, the ejecting means will automatically be retracted a certain distance away from the pierced portion. Since the marketed finger-pricking devices are designed to receive almost any of the also marketed lancets, the apparatus of the invention employs such a finger-pricking device.

In use, the lancet is attached at first to the holding portion (or "holder") of ejecting means in the pricking device, then the protector will be taken off the lancet so that the end cap is successively set on said device. The engagement of the end cap with the pricking device may be effected for example by screwing, snapping or press-fitting the cap into its place. With the end cap attached to the pricking device, lancet body remains until use in its entirety within said cap.

The end cap has the opening f or passing the needle end through it towards the blood-collected body portion, at its end opposite to it other end engageable with the pricking device. It is to be noted that only the protruding needle end of the lancet ejected from the device can advance through the opening, which is at that time in contact with said human body portion. The opening may be of any suitable size and shape, and typically but not delimitedly be a circular hole having a diameter of 3– 5 mm. Such an opening may be formed at and through a flat end surf ace of the end cap, or alternatively at a recessed end surface in another embodiment wherein the recessed surface will be located about 2–3 mm behind the flat end in consideration of the thickness thereof.

As mentioned above, the lancet has the first locking means engageable with the first lockable means formed inside the end cap. The location and shape of the first locking and lockable means are selected such that, when the lancet body and the end cap are attached to the pricking device in this order before use, the first locking means snaps over the first lockable means whereby the said body is retained in the end cap and ready for the blood sampling. However, after use, the first locking means on the lancet body cannot snap back over the first lockable means in the cap. Once the first locking means come into engagement with the first lockable means to set the cap on the device, the lancet body can never slip off said cap through its one end located opposite to the front opening at its one end.

A preferable example of the combination of the first locking and lockable means is as follows. A deformable (for example, flexible or resilient) tapered portion may be formed circumferentially of, inside and integral with, the end cap, so as to provide the first lockable means therein. The tapered portion has (a) surface(s) tapered and extending a proper distance longitudinally of said cap, and each or one of the tapered surfaces has an inner diameter reducing towards the opening so that it may be called a "guiding portion". As for the first locking means, it may be (a) protrusion(s) which is(are) formed on the outer surf ace of the lancet body and whose diameter (that is, the diameter of an imaginary circumcircle of the lancet body, corresponding to the maximum outer diameter of this locking means) is slightly larger than the minimum inner diameter of the tapered portion (i.e., the first lockable means) of the end cap. The first locking means may preferably have at its one side a "guiding portion" facing the opening (and substantially lacks such a portion at its other side).

Although both the first locking and lockable means have the "guiding portions" in the embodiment described, either the locking means or the lockable means (for example only the latter as described above) may comprise such a portion. Alternatively, the first locking means has the "guiding portion", while it is dispensed with for the first lockable means and merely a reduced diameter flange-like portion may instead be formed to protrude from the inner surface of said cap. The most desirable design as to the "guiding portion(s)" may be selected taking into account the deformability (i.e., flexibility or resiliency) of the employed material and the difference between the maximum diameter of the first locking means on the lancet body and the minimum diameter of the first lockable means in the end cap. In a case wherein the difference in diameter is small or the flexibility of the material is high, it is not necessary for both the locking and lockable means are formed with the "guiding portion".

Thus, the end cap can easily be mounted on the pricking device even if the maximum diameter of the first locking means on the lancet body is significantly larger than the minimum diameter of the first lockable means in the end cap. This is because an external force applied to the end cap (e.g., for pushing it towards the device) will cause a slight but sufficient deformation of the first locking and/or lockable means, so that the former is forced to snap over the latter. It is noted in this regard that those locking and lockable means are made of an elastic and flexible material. It is further noted that, after a blood sample will have been taken, the lancet body cannot be withdrawn from the end cap through its end opposite to the front opening. This is because the first locking means abuts at its one side devoid of the tapered portion against the lockable means, and is prevented from snapping over it backward.

Due to such a structure, the end cap retaining therein the lancet body will be disengaged together with said body from the pricking device (whereby the lancet body is pulled out of the holding portion of the ejecting means in said device). In this disengaged state of the end cap, the lancet body cannot be eventually separated therefrom.

It is necessary for the first locking means to come into engagement with at least one portion of the circumferential first lockable means. In other words, if the first lockable means continuously extends around the inner periphery of the end cap, then the locking means need not contact the entirety of the lockable means. Thus, it will suffice that when seen in a plane perpendicular to the direction of ejection two opposite portions (e.g., at regular angular intervals of 180°), four portions (e.g., at said intervals of 90°) or six portions (e.g., at said intervals of 60°) of the lockable means do abut the locking means.

It may also be possible that, contrary to the just described structural feature, the first locking means extends all around the outer periphery of the lancet body so that it can contact a plurality of spaced parts constituting the first lockable means.

In order to ensure the above-described functions of the first locking and lockable means, the lancet and the end cap may preferably be made of a suitable plastics such as a polyethylene or polypropylene, and more desirably, each of them being formed as an integral article. Those materials are also advantageous since they are easy to mold. Preferably, the difference ("DI"–"D2") between the maximum diameter of the locking means (indicated by "D1" in FIG. 2) and the minimum diameter of the lockable means (indicated by "D2" in FIG. 3) may usually be set at about 0.3–0.4 mm.

The apparatus in the invention is constructed such that, as already mentioned above, the lancet body has the arm means whereas the end cap has the second lockable means cooperatable with the arm means. This arm means which has to elastically change and recover its shape may be formed of the same material as the lancet body and integral therewith. The shape and relative positions of those arm means and the second lockable means are as follows. When the lancet body which has been used to take a blood sample is disengaged from the holding, the lancet body is movable a given distance axially of and within the end cap. The arm means will cooperate at that time with the second lockable means so that the needle end is prevented from protruding through and out of the opening of said cap. It is preferable that the arm means and the second locking means are formed integral with the lancet body and the end cap, respectively.

The arm means is provided usually in the form of protrusions extending sideways from the lancet body, and they may be of a rod-like, columnar or wall-like shape. Typically, each of the protrusions is columnar and has a rectangular cross section perpendicular to the direction in which they extend, with the cross section being defined with a pair of longer sides extending peripherally of said lancet body and with a pair of shorter sides extending axially thereof.

Further, each protrusion of the arm means may have at its tip end a curved portion which will reduce the frictional resistance imparted to the arm means by the second lockable means when the lancet body is ejected. In detail, the curved portion may be a transversal columnar portion (being not necessarily of an ideally columnar but partially columnar shape as shown in the drawings, and also including a semi-columnar shape which may be rounded along the inner periphery of the end cap). Alternatively, the curved portion may be of a spherical shape (including a partially spherical shape such as a semispherical one).

In order to ensure the functions of such arm means and second lockable means, the following structural features are preferred herein for them. The second lockable means on the inner surface of the end cap may be a tapered portion extending around it and longitudinally thereof a given distance leading to the front opening and having a diameter reduced towards it. On the other hand, the arm means may be the protrusions whose tip ends forms an imaginary circle having an outer diameter (i.e., the diameter of the circumcircle of the second lockable means) which is equal to an inner diameter of a given cross section of the end cap's tapered portion (with the given cross section being taken by cutting it along a given plane perpendicular to the axis of the end cap).

According to this structure, the arm means is in contact with the second lockable means, which however does not change its shape unless such a strong external force as that imparted when ejecting the lancet body is imparted thereto by the pricking device. Thus, even if the lancet body is made free within the end cap, the engagement of the arm means with second lockable means will hinder the lancet body from advancing beyond a limit (this state being referred to as "stationary state or position" for the sake of convenience). When the strong force is applied for the ejection of lancet body, the arm means contacting the second lockable means will however change its shape due to its elasticity. As a result, the lancet body can move ahead further from the stationary position towards the front opening. The needle end is thus allowed to project through the opening (to thereby pierce the human body portion if it is there for taking a blood sample). Subsequently, the pricking device retracts the lancet body whose needle end has pricked the human body portion, and simultaneously and elastically the arm means recovers its undeformed shape.

In order that the arm means and second lockable means may cooperate in the described manner, the position of one of them relative to the other, the angle of the tapered portion and the height of the protruding arm means must be arranged appropriately taking into account the elastic deformation and the recovery of undeformed shape. This arrangement to ensure the described function of those means would be easy to those who are skilled in the art.

It will be understood that the length and the angle of the tapered portion in the end cap not only affect one another but also depend upon the elasticity and the height of the arm means on the lancet body. The tapered portion usually extends about 8–11 mm axially of the end cap, with said portion being oblique by about 8°–11° relative to the axis of said cap, though not limited to such a dimension. The arm means usually protrude about 1.7–2.0 mm from the outer surface of the lancet body, though not limited thereto, but may vary depending upon their shape and particularly depending upon their material.

The arm means, which are of arm-like members designed to protrude from the lancet body and into contact with the second lockable means, must elastically change their shape so as not to hinder the ejected lancet body from moving towards the front opening (and the human body portion in contact therewith). Therefore, the arm means are made of such an elastic material (e.g., polyethylene or polypropylene) as facilitating their change in shape. Further, the arm means may preferably be oblique relative to the axis of the lancet body, by for example 70°–90°, and more desirably by 90°. This angle refers to an angle measured at a side opposite to the needle end and between each arm-like member and the axis of lancet body.

In another embodiment, the second lockable means may be (a) stepped portion(s) formed in the end cap so as to be substantially equivalent in function to a hypothetical tapered portion whose angle is 90°. Likewise in this modification, the arm means will come into contact with the second lockable means and be elastically deformed to allow the needle end of the ejected lancet body to project out of the opening. After sampling a blood, this arm means (with no external force being applied thereto) also recovers its natural shape to prevent any undesired movement of the lancet body. Instead of the stepped portion as the second lockable means, either a single or a plurality of ridge-like portions can be formed all around or intermittently along the inner periphery of said end cap, on the condition that the ridge-like portion(s) be surely contactable with the arm means.

In a further preferable embodiment, the opening of the end cap is of a shape closely engageable with the lug which, as described above, may be formed at the front extremity of the protector for the needle end. In this case, there is provided a preferable complementary relation between the opening and the lug with respect to their shape and size. It is repeatedly noted here that the lancet body which has been removed from the pricking device after the sampling of blood is able to move a certain distance within the end cap, though the cooperating first locking and lockable means render it unable to slip off through its rear opening facing the device. Therefore, the needle end of the lancet body rocking within the cap is likely to come very close to the opening. The further embodiment described here is advantageous in that the opening is substantially closed with the lug and the interior of the cap is isolated from the exterior. Thus, the used lancet body can be thrown away together with the end cap, much safer than the prior art lancets.

From a different aspect of the present invention, it provides not only the apparatus in its entirety but also separately the lancet and/or the end cap used therein.

THE PREFERRED EMBODIMENTS

The preferred embodiments of the present invention will be described in detail referring to the drawings.

Figure 1:
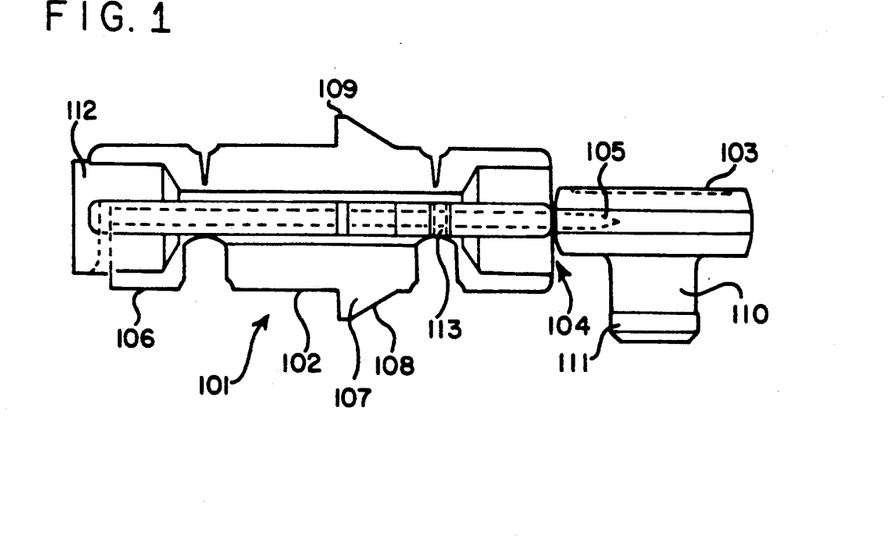
FIG. 1 is a diagrammatic side elevation of a lancet in an embodiment of the invention.
Figure 2:
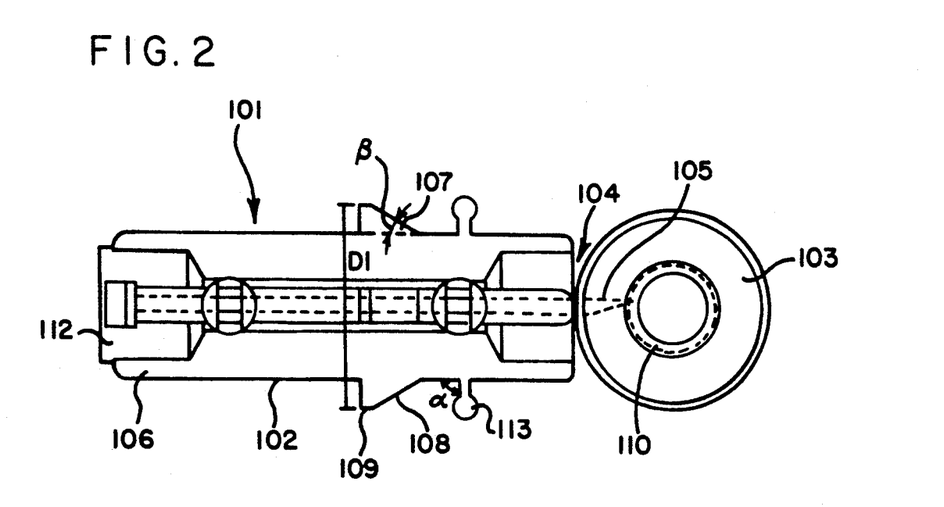
FIG. 2 is a diagrammatic plan view of the lancer.

A lancet 101 in an embodiment is of such a structure as shown with a side view in FIG. 1 and a plan view in FIG. 2. The lancet 101 comprises a lancet body 102 and a needle end 103. The illustrated lancet body 102 and the needle end 103 are formed for example by molding a plastics, and are integral with but separable from one another at 104 in the so-called "twist-off" manner. The lancet body 102 has at its end a needle end 105 jutting forth therefrom. With the protector 103 twisted off the lancet body, the needle end 105 will be exposed to protrude outwardly.

The lancet body 102 is formed with an adapter portion 106 securable to a holding portion (not shown but corresponding to the member 13 in FIG. 19) in the pricking device. The adapter portion 106 is of such a size and shape as press-fittable on said holding portion 13.

Further, the lancet body 102 is provided with a first locking means 107 which is usually called a "guiding member". This guiding member consists of a tapered portion 108 and a non-tapered portion 109, wherein the tapered portion 108 has a diameter reduced towards the needle end 105. The non-tapered portion 109 may however be slightly tapered so long as the first locking means 107 engages with a first lockable means in an end cap and is surely retained therein. In other words, such a slightly tapered portion 109 must not allow the lancet body to be easily withdrawn by pulling its end near an end of said end cap. The non-tapered or slightly tapered portion 109 is defined herein as a member which does not effect the "guiding function". In the illustrated embodiment, the first locking means 107 consists of four pieces disposed at regular angular intervals of 90". Those four pieces may alternatively form an integral member extending all around the periphery of lancet body 102 (to thereassume a conical shape with an oblique surface). More preferably, the first locking means may be composed of for example four, two or more pieces which are spaced apart circumferentially of the lancet body in such a state as arranged in a plane perpendicular to the body's axis at regular intervals of 90° or 180°, respectively, around the needle end's center.

The "guiding" tapered portion 108 of the first locking means 107 acts in a desirable manner, and particularly cooperates with the first lockable means formed in the end cap as described later so that it can smoothly be attached to the pricking device. Thus, the first lockable means shapes over the first locking means 107 whereby the lancet body advances forward a distance to take its position ready for the sampling of blood. On the other hand, as the lancet body is retracted after the sampling, the non-tapered "non-guiding" portion 109 will collide with the first lockable means of the end cap. In this way the lancet body is securely retained within the end cap while and even after the cap is pulled off the pricking device so as to disengage said body from the holding portion of said device.

The lancet body 102 further comprises an arm means 113 which in the illustrated example is composed of columnar members jutting substantially perpendicular to and side ways from the lancet body 102. As described above, the arm means need not be strictly perpendicular to said body, but their surfaces not facing the needle end may extend at an angle ("alpha" in FIG. 2) of for example about 70°-90°, or greater than 90° a little, but more preferably go, relative to the axis of the lancet body. The thickness (i.e., length along said axis), the peripheral length, as well as the height (i.e., the distance between each member' summit and the outer surface of the body) of said means may be designed appropriate in view of the material property in order to adjust their deformation and recovery.

For the lancet for use with the conventional pricking device is, or the arm means or its constituent members are, 0.6–0.8 mm in thickness, 1.3–1.6 mm in length and 1.7–2.0 mm in height. The tip end of each illustrated member of the arm means 113 is of a columnar shape.

Although two constituent members of illustrated arm means 113 are disposed around the lancet body at regular intervals of 180°, more members may constitute the means, provided that the second lockable means can cooperate with said arm means so that the end cap may fully enclose the needle end which has pierced the human skin for the sampling of blood. In preferable examples, four members as illustrated or two members are formed around the lancet body respectively at regular intervals of 90° or 180° about the center of the needle end, when seen in a plane perpendicular to the lancet body. The number of the constituent members must be reconciled with the deformability and must not render it difficult to eject the molded lancet body out of a molding apparatus.

The protector 103, which is formed integral with the lancet and protects the needle end, preferably has a lug 110 fittable in the opening through the end cap. In the illustrated example, the lug 110 is slightly enlarged in diameter at a region adjacent to its end surface. In order to retain in place the lug once fitted in the opening, the "snap-fitting" is more preferable than "pressfitting" though the latter is also employable.

Figure 3:
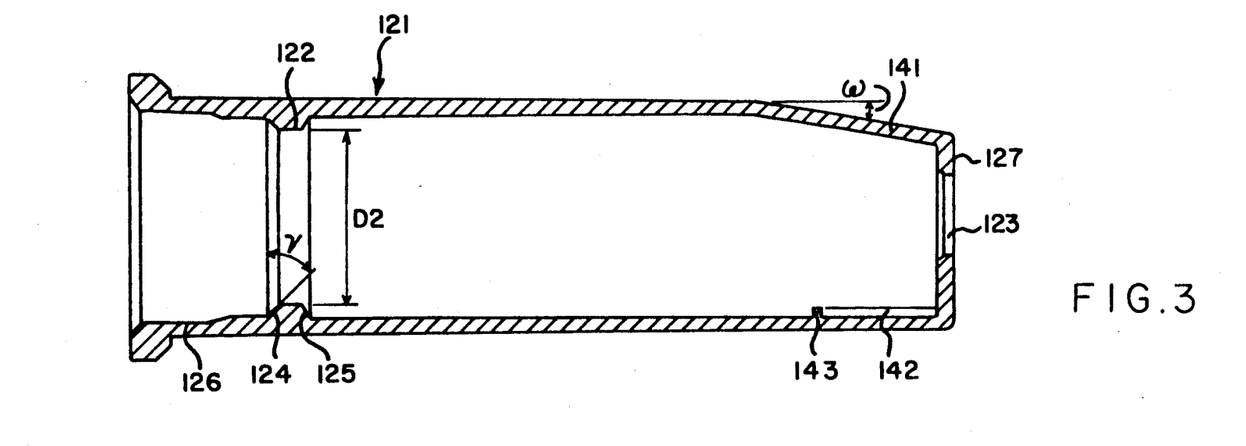
FIG. 3 is a cross section of an end cap employed in the embodiment.

The end cap 121 is of a structure in its longitudinal cross section as schematically shown in FIG. 3, and has in its interior the first lockable means 122 disposed inside as well as the opening 123 as referred to above. When the end cap is attached to the pricking device already carrying the lancet body 102, the first locking means 107 can snap over the first lockable means 122 and be accommodated in the end cap, by virtue of the position and shape of said lockable means. In this connection, the first lockable means 122 is preferably formed with a similar "guiding" tapered portion 124 facing the aforementioned tapered portion 108 of the lancet body. With the end cap being set in place, the first lockable means 122 must be either in contact with or adjacent to the non-tapered portion 109 of the first locking means 107.

By providing both the lancet body and the end cap with the tapered portions 108 and 124, respectively, the first locking means 107 of said body can smoothly click over the first lockable means 122 of said cap and further advance towards the opening 123.

The angle of the end cap's tapered portion 124 of the lockable means (i.e., the angle of its inclined surface) may be altered appropriate corresponding to the angle of the lancet body's tapered portion 108 of the locking portion. A further factor which is to be taken into account for this purpose are the materials of the end cap and the lancet body, particularly their locking and lockable means. A still further factor is the difference between the maximum outer diameter of the locking means and the minimum inner diameter of the lockable means. In any case, the lancet body's locking means must click over the lockable means in the end cap which is then being engaged with the pricking device, but must not move backward beyond the lockable means after the blood sample has been taken. Generally, the angle ("beta" in FIG. 2) of the tapered portion of the first locking means is about 20°–35°, with an angle about 45°–50° being chosen for the inclination of the lockable means' tapered portion. For example, the angle (indicated by "gamma" in FIG. 3) of the tapered portion 108 is 30° for the locking portion, and the angle of the cooperating tapered portion 124 is 45° for the lockable portion.

A side 125 of the lockable means, which will engage with the non-tapered portion 109 of the locking means 107, is preferably not tapered to prevent the lancet body from slipping off the cap. However, the integral molding of the end cap may be facilitated by the side 125 inclined at a small angle (e.g., 45°–50°). The same will apply also to the non-tapered portion 109 of the lancet body.

As will be apparent from the foregoing, both or either of the first locking and lockable means may be formed with their one sides tapered for the smooth initial snapping of the former over the latter. In order to stop the former not to move backward beyond the latter and thus to retain the used lancet body in the end cap, both or either of the first locking and lockable means may be formed with their other sides not tapered. Any of those options can be taken herein in due consideration of the difference in diameter between said first means, the material forming said members and the angle of said tapered portions.

The end cap 121 has a fastenable portion 126 opposite to the opening 123, with the portion 126 serving as a means to fix the end cap on the pricking device. In an example shown in FIG. 3, the fastening portion 123 is of a shape complementing the pricking device such that the former can be press-fitted on the latter. Alternatively, the end cap may be threaded to the device by means of their screw-thread portions (as shown in FIGS. 5-8), or be snapped on the device.

The end cap in the apparatus of the invention further comprises a second lockable means. This lockable means in an example shown in FIG. 3 is a tapered portion disposed near an end surface of the end cap, and the tapered portion is inclined relative to the axis of said cap at an appropriate angle ("omega" in FIG. 3). This angle depends on the shape and the like of the arm means, and is usually from about 8°–11°. The arm means 113 has to engage with any of the second lockable means' portions extending longitudinally of the lancet body.

In detail the inner diameter of cross section of the end cap gradually reduces towards the opening so that the arm means can touch any predetermined portion of the end cap's oblique inner periphery. The lancet body, to which no force or a very weak force is applied, cannot advance beyond that predetermined portion. If a significant force is applied to the lancet body, then the arm means 113 will be pressed to the end cap's inner surface and deformed to an extent which corresponds to the strength of said force. Consequently, the contact portion of the oblique periphery will shift to the right in FIG. 3.

A stepped portion 142 (shown by the broken line in FIG. 3) or a weir-shaped portion 143 may be formed, as the second lockable means, on the inner periphery of the end cap. An lower half of FIG. 3 shows a different example than the example of the second lockable means shown in an upper half of FIG. 3.

The end cap comprises at its end the opening 123 opposite to the fastenable portion 126. This opening 123 permits the needle end of the ejected lancet body, however in a preferable example it can be tightly closed with the lug of the protector which will be separated from the used lancet. Although the arm means of lancet body detached from the pricking device's holding portion does cooperate with the second lockable means and prevents the needle end from remaining exposed, it is more desirable to shut the lancet body's needle end up in the used end cap having the opening closed with the lug. The safety of this apparatus is ensured in this manner, and any dangerous incident can be avoided. The end plane 127 including the opening 123 coincides with the cap's tip end in the example shown in FIG. 3, but it may be recessed therefrom by for instance about 2-3 mm to thereby provide a dam-like protrusion, if necessary.

Such a dam-like protrusion will eliminate the possible problems caused by a blood drop which appears around the pierced cut and tends to stick to the end plane 127 when the pricking device is used. The blood drop on the tip end plane 127 will occasionally be transferred to the skin of an operator, for instance a nurse who has used this apparatus for the blood sampling. This incident will however scarcely take place with the recessed end plane. In addition, another danger of carelessly touching the bloodstained needle will also be diminished, because the used needle which would rarely remain exposed through the opening does not jut beyond the dam-like protrusion at the cap's extremity.

Further, the dam-like protrusion is useful to control the pressure applied to the skin portion so that the congestion can be intensified or lowered. The adjustment of collected amount of blood will also be easier, since the change in the stuffed degree of skin portion in the recess encircled with dam-like protrusion does contribute to the change in the depth of the cut or wound formed with the needle end.

The operation of the apparatus will now be summarized below with reference to FIGS. 4 to 8.

Figure 4:
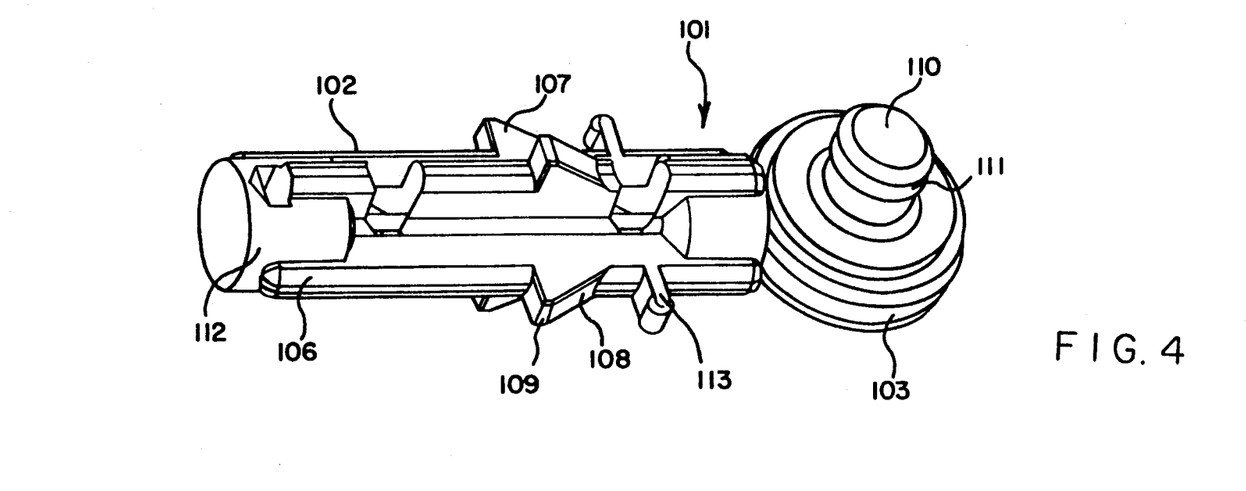
FIG. 4 is a diagrammatic perspective view of the lancet in the embodiment.

The lancet 101 for use to collect blood samples is offered in the state whose perspective view is shown in FIG. 4. The fastenable portion 106 of the lancet body in this sate is forced onto the holding portion (similar to the member 13 in FIG. 10) in the pricking device. Then, the protector 103 is twisted off the lancet so that the needle end 105 is exposed.

Figure 5:
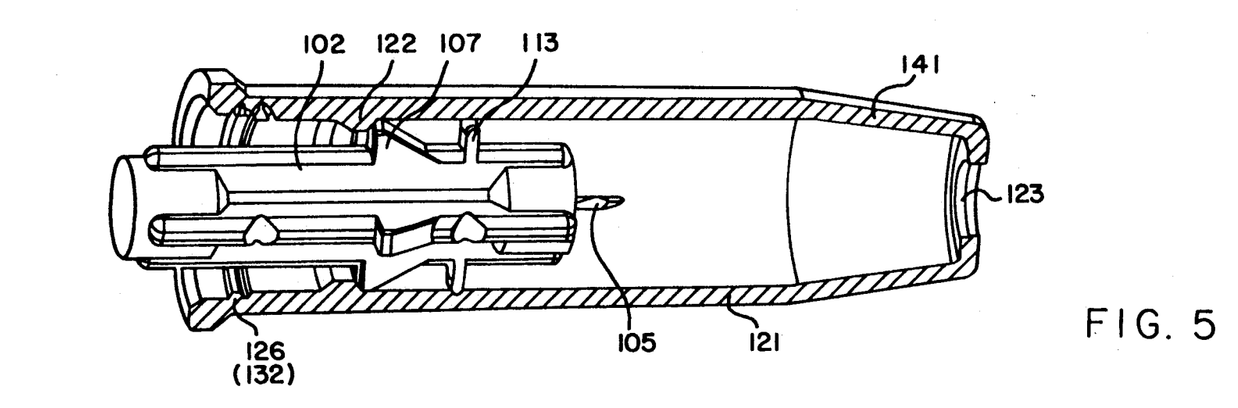
FIG. 5 is a perspective view showing diagrammatically but partly in cross section a blood collecting apparatus, with the apparatus being in use and at a step therein.

Subsequent to this step, the end cap 121 is threaded at its threaded portion 132 onto the pricking device (not shown in FIG. 5). As is shown in FIG. 5, which is a perspective view showing those members partly in cross section, the first locking means 107 of the lancet body will accordingly snap over the first lockable means 122 in the end cap. Those members in this state are ready to collect a blood sample. Although the locking means 107 is illustrated to be in contact with the lockable means 122, the former may stand apart from but at the right of the latter.

Figure 6:
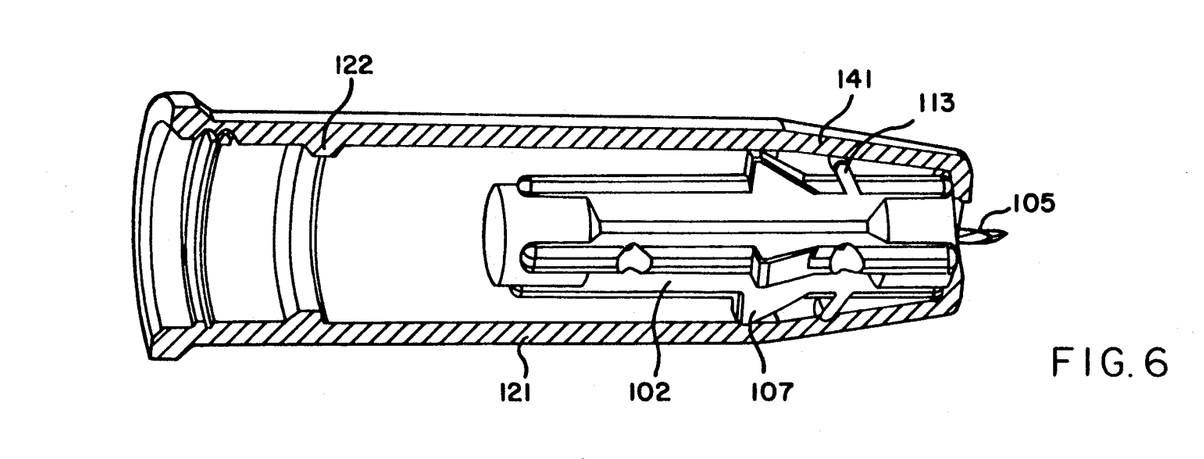
FIG. 6 is a perspective view showing diagrammatically and partly in cross section the apparatus in use and at another step.

Thereafter, the end surface of the cap is urged toward the skin portion (not shown) where the blood sample is to be taken, before the lancet body is unlocked and ejected. As seen in FIG. 6 showing the ejected lancet body 102 which has pierced the skin portion, the arm means are in a tight engagement with the tapered portion of the end cap and are slanting backward due to their elasticity (thus reducing the angle "alpha"). Such a deformation of the arm means enables the projection of the needle end through the opening, and the needle end pricks without any difficulty the skin portion.

Immediately after piercing the skin portion, the lancet body is retracted by the pricking device so as to return to its home position away from the skin portion, with the arm means also recovering their undeformed shape.

At a further step, the end cap 121 is detached from the pricking device 131 by rotating the former relative to the latter to loosen the threaded portion 132 and by subsequently pulling the former away from the latter. During this operation, the non-tapered portion 109 of the first locking means 107 will collide with the non-tapered portion 125 of the first lockable means 122, as shown in FIG. 5. Since at least one of the locking and lockable means (or both, as in the illustrated embodiment) lacks the "guiding portion", the former 107 cannot snap over the latter 122. Thus, by forcibly pulling the end cap 121 away from the pricking device 131, the lancet body 102 will be removed automatically from the holding portion 133 provided in said device.

Figure 7:
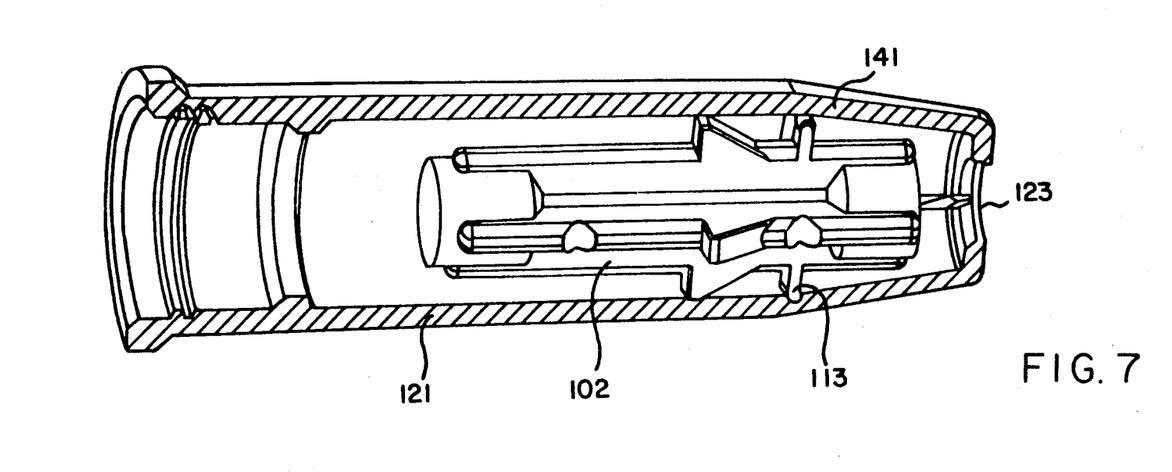
FIG. 7 is a similar perspective view of the apparatus in use and at still another step.

In this state shown in FIG. 5, the first locking means 107 is stopped by the first lockable means 122 so as to "lock" the lancet body 102 in place not to slip off the end cap 121. It will also be seen in FIG. 5 that the arm means which have restored their natural shape will, due to a possible forward displacement, contact and be stopped by a different portion of the slanted second lockable means. FIG. 7 shows that this different portion is on the left of the initial portion shown in FIG. 5. In a case wherein the lockable means is of a stepped shape or weir-like shape, the displaced arm means will contact the same portion of the lockable means as it has originally done. In any event, since the needle end will never project again from the end cap through its opening, the danger of carelessly touching the needle end is diminished to a remarkable degree.

Figure 8:
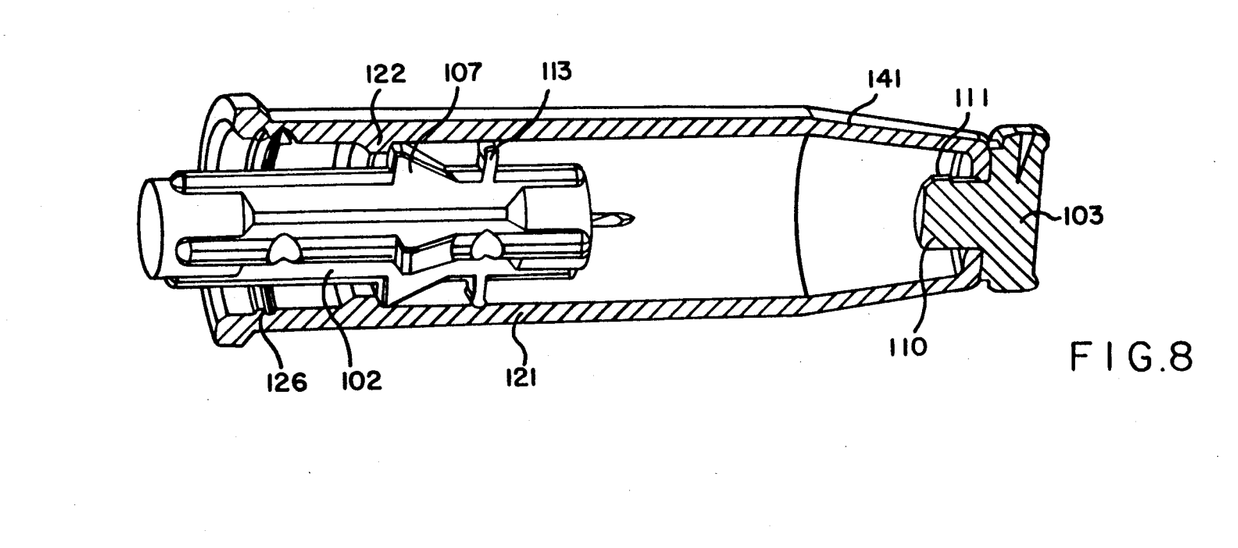
FIG. 8 is also a perspective view of the apparatus after use and in its discarded state.

FIG. 8 shows in cross section the members other than the lancet body 102 and illustrates a state of the needle protector 103 and its lug 110, which is "press-fitted" in the opening 123 in this case so as to plug it. The plugging of said opening may preferably precede the disengagement of the end cap 121 from the pricking device, whereby the used needle end of the lancet body can never advance into the opening to cause the aforementioned danger.

Although the state shown in FIG. 7 can not perfectly preclude the danger of touching the needle end, the improved state in FIG. 8 is free from said danger and enables a safer discarding of the used lancet body enclosed with the end cap. FIG. 8 indicates a still further important feature that the cross section of the protector is equal to or larger than the end plane 127 of the cap, so that with the 110 being fitted in the opening 123, the protector may cover perfect the plane which will probably carry a blood residue as the cause of the aforementioned danger.

In summary, the apparatus of the invention affords the following advantageous:

(1) that similarly to the prior art lancet used with the finger-pricking device the lancet in the invention can be mounted on the device before covered with the end cap and made ready to take a blood sample, and after use, the lancet can be discarded safe because by simply detaching from the device the lancet body is kept in the cap and thus the needle end is hindered from being touched;

(2) that due to its simple structure the end cap can be manufactured easily and at a so lower cost that any economic problem does not arise even if it were thrown away together with the lancet body;

(3) that the lancet as well as the end cap in the invention can be used in combination with the prior art finger-pricking device; and (4) that in the preferable embodiment the lug as an integral portion of the needle protector may be fitted in and seal up the opening of the cap so that the lancet body within it is isolated from the exterior, and at the same time the residual blood probably sticking to the cap's end is also prevented from staining any object or human body, thus improving the safety of the apparatus.

The scope of the present invention is not restricted to the aforedescribed embodiments but may be modified in various manner without departing from the spirit of the invention.

What is claimed is:

1. A blood collecting apparatus for use with a lancet ejector of the type having an ejecting means which includes a spring means and a holding portion for coupling to a lancet assembly, the spring means being in a compressed state before ejection, the spring means being related and extended to propel the holding portion and the lancet assembly, and the spring means retracting to retract the holding portion and the lancet assembly after ejection, the blood collecting apparatus comprising, in combination:

a lancet assembly comprising a needle and an integrally molded lancet body, the needle having a point, the lancet body defining an axis and having an adapter portion and a needle end, the needle extending from the needle end, and the adatper portion being releasably attachable to the holding portion of the lancet ejector, the lancet body comprising first locking means, the first locking means being molded with the lancet body and extending radially therefrom in a plane substantially perpendicular to the axis of the lancet body to provide a guiding member, and locking arm means, the locking arm means being elastically yieldable such that the locking arm means deforms when the spring means is released and extended to allow the lancet assembly to be propelled forward and the locking arm means recovers its original shape when the spring means retracts to retract the lancet assembly after ejection, an end cap having a distal end, an open proximal end, and an axially extending internal cavity having an inner wall and cooperating with the open proximal end, the open proximal end being releasably attachable to said lancet ejector, the distal end having an axially extending opening, the end cap being adapted to cover and protect the lancet body and needle such that the lancet assembly is disposed within the internal cavity when the lancet assembly and the end cap are attached to the lancet ejector, the needle point advancing outward through the opening when the lancet is propelled through the end cap, the end cap comprising a first lockable means adapted to cooperate with the first locking means on the lancet body to prevent the lancet body from slipping out the open proximal end of the end cap when the end cap is detached from the lancet ejector, the first locking means being integrally molded in the end cap and extending substantially radially inward from the inner wall of the end cap, and a second lockable means adapted to engage the arm means of the lancet body to prevent the needle point from accidentally protruding out of the opening in the open proximal end of the end cap.

2. The blood collection apparatus of claim 1 wherein the lancet assembly further comprises a protector detachably molded to the needle end of said lancet body, said protector encasing the needle point and having a detachable lug portion.

3. The blood collection apparatus of claim 2 in combination with a lancet ejector adapted to hold said lancet body and to propel said needle end to pierce a human body portion.

4. The blood collection apparatus of claim 1 wherein said second lockable means comprises a tapering of the inner wall of the end cap to a smaller diameter adjacent the distal end of said cap, and adapted to engage said arm means and restrict accidental axial movement of said lancet body toward said distal end after blood has been drawn.

5. The blood collection apparatus of claim 1 wherein said second lockable means comprises a protrusion molded to the inner wall of said end cap and extending radially inwardly in a position to engage said arm means and restrict accidental axial movement of said lancet body toward the distal end of said end cap after blood has been drawn.

6. The blood collection apparatus of claim 1 wherein said first lockable means comprises four solid guiding members disposed at 90 degree angular intervals circumferentially around said body, each guiding member comprising a tapered portion tapered inwardly toward the needle end of said lancet body and a substantially non-tapered portion disposed at the opposite end of said means.

7. The blood collection apparatus of claim 1 wherein said locking arm means comprises at least two members extending substantially radially from said lancet body.

8. A molded lancet body for use in a blood sampling apparatus comprising:
(a) a lancet body rigidly holding an axially disposed needle and adapted to be releasably attachable to a lancet ejector, said body means comprising a nonflexible first locking means molded as a part of said lancet body which provides a guiding member and extends radially from said body in a plane perpendicular to said body's axis; and
(b) locking arm means molded as a part of said lancet body and extending radially therefrom in a plane substantially perpendicular to the body's axis and adapted to be elastically yieldable to allow said needle to be propelled toward a human body portion to pierce same, and to elastically recover its undeformed shape and position when the propelling force is withdrawn from said body.

* * * * *

UNITED STATES PATENT AND TRADEMARK OFFICE
CERTIFICATE OF CORRECTION

PATENT NO. : 5,314,442
DATED : MAY 24, 1994
INVENTOR(S) : SUSUMU MORITA

It is certified that error appears in the above-identified patent and that said Letters Patent is hereby corrected as shown below:

Column 4, line 24, delete "all" and substitute therefor -- are --;

Column 9, line 18, delete "lancer" and substitute therefor -- lancet --;

Column 9, line 35, delete "lancer" and substitute therefor -- lancet --; and

Column 10, line 22, delete "shapes" and substitute therefor -- snaps --.

IN THE CLAIMS:

Column 14, line 64, delete "related" and substitute therefor -- released --.

Signed and Sealed this

Thirteenth Day of December, 1994

Attest:

BRUCE LEHMAN

Attesting Officer

Commissioner of Patents and Trademarks